United States Patent
Wu et al.

(10) Patent No.: US 9,005,405 B2
(45) Date of Patent: Apr. 14, 2015

(54) EXTRACTIVE DISTILLATION PROCESS FOR BENZENE RECOVERY

(75) Inventors: Kuang-Yeu Wu, Plano, TX (US);
Tzong-Bin Lin, Chia-Yi (TW);
Fu-Ming Lee, Katy, TX (US);
Tsung-Min Chiu, Taipei (TW);
Jeng-Cheng Lee, Chia-Yi (TW)

(73) Assignees: CPC Corporation, Taiwan, Taipei (TW); AMT International, Inc., Plano, TX (US)

( * ) Notice: Subject to any disclaimer, the term of this patent is extended or adjusted under 35 U.S.C. 154(b) by 503 days.

(21) Appl. No.: 13/410,286

(22) Filed: Mar. 1, 2012

(65) Prior Publication Data

US 2013/0228447 A1  Sep. 5, 2013

(51) Int. Cl.
*B01D 3/40* (2006.01)
*C07C 7/08* (2006.01)
*C07C 15/04* (2006.01)

(52) U.S. Cl.
CPC ... *B01D 3/40* (2013.01); *C07C 7/08* (2013.01); *C07C 15/04* (2013.01)

(58) Field of Classification Search
CPC ............ B01D 3/40; C07C 7/08; C07C 15/04
USPC ......................... 203/43, 57, 81, 82
See application file for complete search history.

(56) References Cited

U.S. PATENT DOCUMENTS

| | | | |
|---|---|---|---|
| 3,361,664 A | 1/1968 | Broughton | |
| 3,396,101 A | 8/1968 | Broughton | |
| 3,537,984 A * | 11/1970 | Thompson | 208/321 |
| 3,544,453 A * | 12/1970 | Thompson | 208/321 |
| 4,048,062 A | 9/1977 | Asselin | |
| 4,057,491 A * | 11/1977 | Bushnell et al. | 208/321 |
| 4,081,355 A | 3/1978 | Preusser | |
| 4,586,986 A * | 5/1986 | Preusser et al. | 203/22 |
| 4,664,783 A | 5/1987 | Preusser | |
| 4,693,991 A * | 9/1987 | Bjornson et al. | 502/220 |
| 5,031,754 A | 7/1991 | Emmrich | |

(Continued)

FOREIGN PATENT DOCUMENTS

| | | |
|---|---|---|
| CN | 101081993 | 4/2010 |
| GB | 1139630 | 1/1969 |

(Continued)

*Primary Examiner* — Nina Bhat
*Assistant Examiner* — Jonathan Miller
(74) *Attorney, Agent, or Firm* — Cascio & Zervas

(57) ABSTRACT

Recovering high purity benzene from hydrocarbon feedstock containing aromatics and non-aromatics is implemented by simple and low-cost modifications to conventional extractive distillation columns (EDCs). Methyl cyclohexane (MCH) that is generated through non-selective hydrogenation of toluene in hydrodesulfurization (HDS) units is a major contaminant in benzene production. To meet MCH specifications, often times the extractive distillation (ED) process for recovering purified benzene is operated with excessive benzene loss to the overhead raffinate stream, producing a lower quality non-aromatic product. Novel techniques (1) remove operational constrictions of the HDS unit on MCH production, thus lengthening the catalyst life and (2) allow the EDC to drive essentially any amount of MCH away from the bottom benzene product without concerns with benzene loss to the overhead raffinate stream and (3) recover benzene from the overhead raffinate stream to upgrade the quality of non-aromatic product and increase the benzene product recovery.

24 Claims, 3 Drawing Sheets

(56) References Cited

U.S. PATENT DOCUMENTS

| | | | |
|---|---|---|---|
| 5,215,629 A | | 6/1993 | Skatulla |
| 5,252,200 A | | 10/1993 | Skatulla et al. |
| 6,007,707 A | * | 12/1999 | Donnermeyer et al. ...... 208/313 |
| 8,362,314 B2 | * | 1/2013 | Stabel et al. .................. 585/862 |
| 8,378,164 B2 | * | 2/2013 | Stabel et al. .................. 585/865 |
| 2010/0300830 A1 | * | 12/2010 | Noe et al. ........................ 196/98 |
| 2012/0273392 A1 | * | 11/2012 | Serban et al. ................... 208/63 |

FOREIGN PATENT DOCUMENTS

| | | |
|---|---|---|
| GB | 1274380 | 5/1972 |
| GB | 1283180 | 7/1972 |
| GB | 1291029 | 9/1972 |
| GB | 1309875 | 3/1973 |
| GB | 1432690 | 4/1976 |
| TW | 438882 | 2/2000 |
| WO | 9911740 | 3/1999 |

* cited by examiner

EXTRACTIVE DISTILLATION PROCESS FOR BENZENE RECOVERY

FIELD OF THE INVENTION

The present invention is directed to improved processes for recovering high purity benzene from hydrocarbon feedstock that contains aromatics and non-aromatics where the processes can be implemented with minimal modifications to conventional extractive distillation columns in current benzene recovery extractive distillation processes.

BACKGROUND OF THE INVENTION

Commercial extraction processes for aromatic hydrocarbon recovery typically involves hydrotreating feedstock in a hydrodesulfurization unit to remove sulfur and nitrogen before undergoing extractive distillation (ED) with a non-aqueous selective solvent to produce a high purity benzene product. For example, U.S. Pat. No. 5,215,629 to Skatulla et al. discloses an ED process that uses non-aqueous N-substituted morpholine solvent to separate aromatics from mixtures containing non-aromatics that entails distilling a raffinate (non-aromatics) stream from the overhead of an extractive distillation column (EDC) in a separate distillation column. U.S. Pat. No. 5,252,200 to Skatulla et al. simplifies the configuration and operation of the '629 patent process by including the feature of distilling the raffinate (non-aromatics) stream from an overhead of the EDC in an internal distillation column that is installed on top of the EDC to recover a selective solvent residue from the raffinate. The distillation column is installed as an integral upper portion of the EDC for recovery of the selective solvent residue from the overhead raffinate stream.

Hydrotreatment of feedstock generates methyl cyclohexane (MCH) through non-selective hydrogenation of toluene. Since MCH is one of the major contaminants in the final benzene product, the hydrodesulfurization (HDS) unit is operated under stringent conditions in order to maintain the required balance between removing sulfur and nitrogen contaminants and minimizing the formation of MCH. Consequently, in order to meet MCH specifications for benzene products, the ED operates under process conditions that result in excessive benzene loss to the overhead raffinate stream and yields lower quality non-aromatic products.

SUMMARY OF THE INVENTION

The present invention is based in part on the recognition that current extractive distillation processes, as exemplified by U.S. Pat. No. 5,252,200, for recovering benzene from feedstock such as the $C_6$ fraction of hydrotreated coal tar, are deficient in many respects. The deficiencies can be attributed to the accumulation of MCH in the raffinate distillation column. The MCH is pushed downward toward the lower portion of the EDC and contaminates the benzene that is present in the rich solvent at the bottom. To prevent MCH from descending into the column, the EDC reboiler duty can be increased but this causes additional benzene loss to the overhead raffinate stream and higher energy consumption in the EDC. A related problem is the small loading that is in the upper EDC and the integral raffinate distillation column, especially above the EDC solvent feed tray, which is caused by the low non-aromatic content in the feed. Consequently, a high external reflux is required to prevent channeling which would otherwise lead to low column efficiency in the upper portion of the integrated EDC. This is the case even when employing a top distillation column with a reduced diameter.

The present invention provides improved methods for processing the raffinate stream that is produced at the top of the EDC in order to minimize benzene loss to the raffinate product and to prevent (or minimize) MCH from contaminating the benzene product at the bottom of the EDC. The inventive techniques can be realized by simple and low-cost modifications to conventional extractive distillation columns. One feature of the invention eliminates the requirement of limiting MCH generation in the HDS unit; this accomplished by improved operations in the subsequent purification processes that improve the separation between MCH and benzene. The HDS unit operation is more flexible and, as a result, the HDS catalyst life can be significantly increased as the HDS unit is configured to focus on the removal of thiophene (another benchmark contaminant) and other sulfur and nitrogen compounds. Other features of the invention are the reduction of MCH contaminants in the benzene product, reduction of benzene loss to the non-aromatic product to maintain its quality as a gasoline blend stock, increased recovery of the benzene product, and reduced energy consumption of the purification process. Extractive distillation (ED) is the preferred process for separating benzene from the non-aromatics, including MCH and uses solvent such as N-substituted morpholines with substituents containing not more than 7 carbon atoms, sulfolane, glycols, N-methyl pyrrolidone and their mixtures, all with or without water. Preferred solvents are N-formyl morpholine (NFM) and sulfolane/water mixture containing 0 to 1.0% water; a particularly preferred solvent is non-aqueous NFM.

Accordingly, in one aspect, the invention is directed to a process for recovering high purity benzene from a feedstock containing aromatic hydrocarbons and non-aromatic hydrocarbons that includes the steps of:

(a) removing sulfur and nitrogen contaminants from the feedstock through a hydrodesulfurization (HDS) unit to yield a hydrotreated feedstock;

(b) introducing the hydrotreated feedstock into in a distillation column to remove a heavy portion of the hydrotreated feedstock and to recover a $C_6$ fraction and lighter portion of the hydrotreated feedstock that contains benzene which is introduced to a middle portion of an extractive distillation column (EDC);

(c) introducing a lean solvent stream that is recycled from the bottom of a solvent recovery column (SRC) into an upper portion of the EDC as a selective solvent feed;

(d) recovering a first non-aromatic hydrocarbon-rich stream from the top of the EDC and withdrawing a first solvent-rich stream containing the solvent and substantially all the benzene that was present in the $C_6$ fraction and lighter portion of the hydrotreated feedstock from the bottom of the EDC;

(e) introducing the first solvent-rich stream into a middle portion of the SRC and recovering an aromatic hydrocarbon stream consisting essentially of benzene and that is substantially free of the solvent and non-aromatic hydrocarbons from the top of the SRC and removing the lean solvent stream from the bottom of the SRC;

(f) introducing the first non-aromatic hydrocarbon-rich stream from step (d) into a lower portion of a liquid-liquid extraction (LLE) column and introducing a slip stream from the lean solvent stream from step (c) into an upper portion of the LLE column as the solvent feed stream;

(g) recovering a second non-aromatic hydrocarbon-rich stream from the top of the LLE column as a raffinate product and removing a second solvent-rich stream from the bottom of the LLE column, which is recycled into the middle portion of the EDC; and, optionally, (h) introducing a stripping agent into a lower portion of the EDC to prevent channeling in an upper portion of the EDC that is caused by low column loading to thereby enhance its separation efficiency.

In another aspect, the invention is directed to a process for recovering high purity benzene from a feedstock containing aromatic hydrocarbons and non-aromatic hydrocarbons that includes the steps of:

(a) removing sulfur and nitrogen contaminants from the feedstock through a hydrodesulfurization (HDS) unit to yield a hydrotreated feedstock;

(b) introducing the hydrotreated feedstock into a distillation column to remove a heavy portion of the hydrotreated feedstock and to remove a $C_6$ fraction and lighter portion of the feedstock which is introduced into a middle portion of an EDC which contains a raffinate distillation column as an integral upper portion of the EDC for recovering benzene from ascending raffinate vapor stream to provide an internal reflux for the EDC;

(c) introducing a lean solvent stream recycled from the bottom of a solvent recovery column (SRC) into an upper portion of the EDC below the raffinate distillation column as a primary selective solvent feed;

(d) introducing a slip stream from the primary selective solvent stream to the upper portion of the raffinate distillation column in step (b) as a secondary selective solvent feed to convert the raffinate distillation column into an auxiliary EDC to recover additional benzene from the first non-aromatic hydrocarbon-rich stream;

(e) recovering a first non-aromatic hydrocarbon-rich stream that is low in benzene content from the top of the EDC and withdrawing a first solvent-rich stream containing the solvent and substantially pure benzene from the bottom of the EDC;

(f) introducing the first solvent-rich stream into a middle portion of the SRC, recovering an aromatic hydrocarbon stream containing essentially pure benzene, that is substantially free of the solvent and non-aromatic hydrocarbons, from the top of the SRC, and removing the lean solvent stream from the bottom of the SRC;

(g) introducing the first non-aromatic hydrocarbon-rich stream into a middle portion of a distillation column to recover a second non-aromatic hydrocarbon-rich stream from the top of the distillation column as a raffinate product, and to remove a bottom stream from said distillation column containing benzene, non-aromatic hydrocarbons and entrained solvent, which is recycled to the EDC as a mixture with the EDC primary solvent feed stream; and optionally, (h) introducing a stripping agent to the lower portion of the EDC to prevent channeling in an upper portion of the EDC caused by low column loading, to increase its separation efficiency.

The invention can be readily implemented by revamping existing ED processes for benzene recovery from coal tar or other similar feedstocks. The only additions to the existing equipment are a small LLE column and a gas blower (optional), or a small distillation and a gas blower (optional), along with some process piping modifications.

DETAILED DESCRIPTION OF THE PREFERRED EMBODIMENTS

Figure 1:
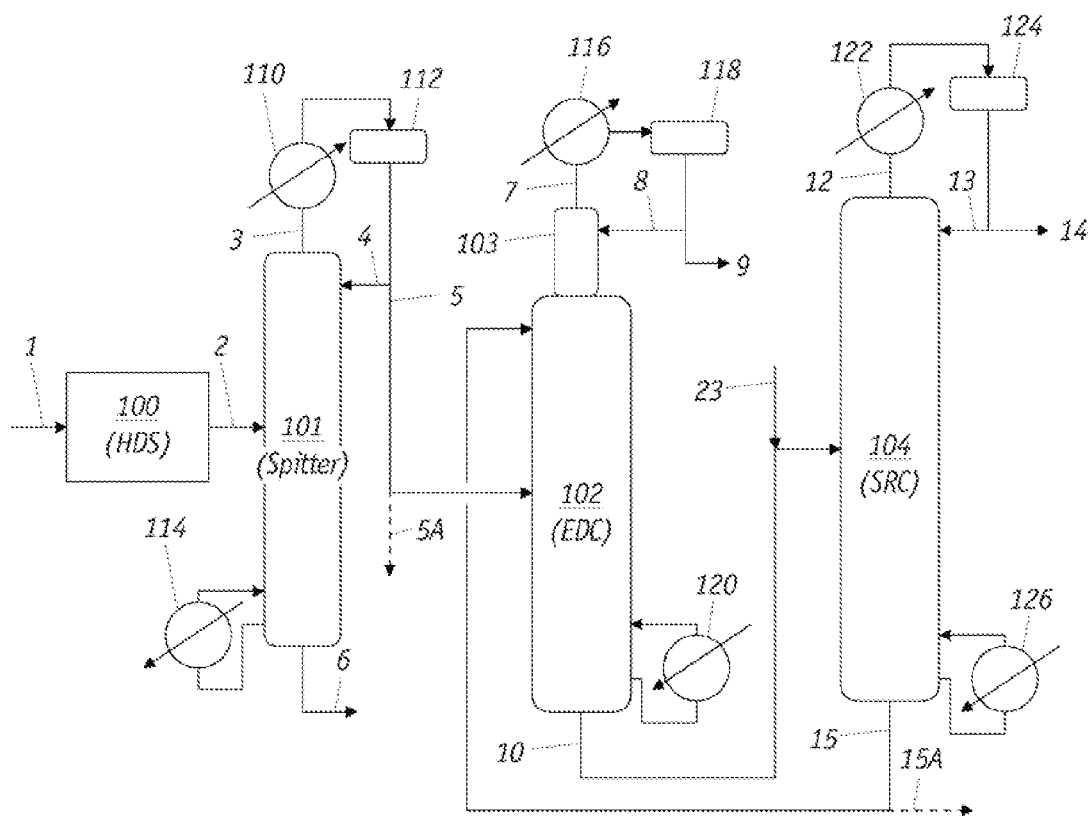
FIG. 1 is a schematic diagram of an extractive distillation (ED) process using NFM solvent for benzene recovery.

FIG. 1 illustrates a commercial process, for producing high purity benzene and non-aromatic hydrocarbons for gasoline blending or other applications, which employs a HDS unit 100, a splitter column 101 that is equipped with reboiler 114, an integrated EDC 102 that is equipped with reboiler 120, and a solvent recovery column (SRC) 104 that is equipped with reboiler 126. In operation, a suitable hydrocarbon feed such a light fraction of coal tar containing mainly benzene, toluene and $C_6$-$C_7$ non-aromatic hydrocarbons is fed via line 1 into a HDS unit 100. The hydrosulfurization process removes sulfur and nitrogen contaminants in the fraction but also generates MCH so, in a conventional benzene recovery process, HDS unit 100 is operated under conditions that remove the sulfur and nitrogen contaminants and, at the same time, minimize the formation MCH. MCH is the major contaminant in the benzene product, which is typically kept below 1,000 ppm and preferably below 200 ppm in the final product.

Figure 2:
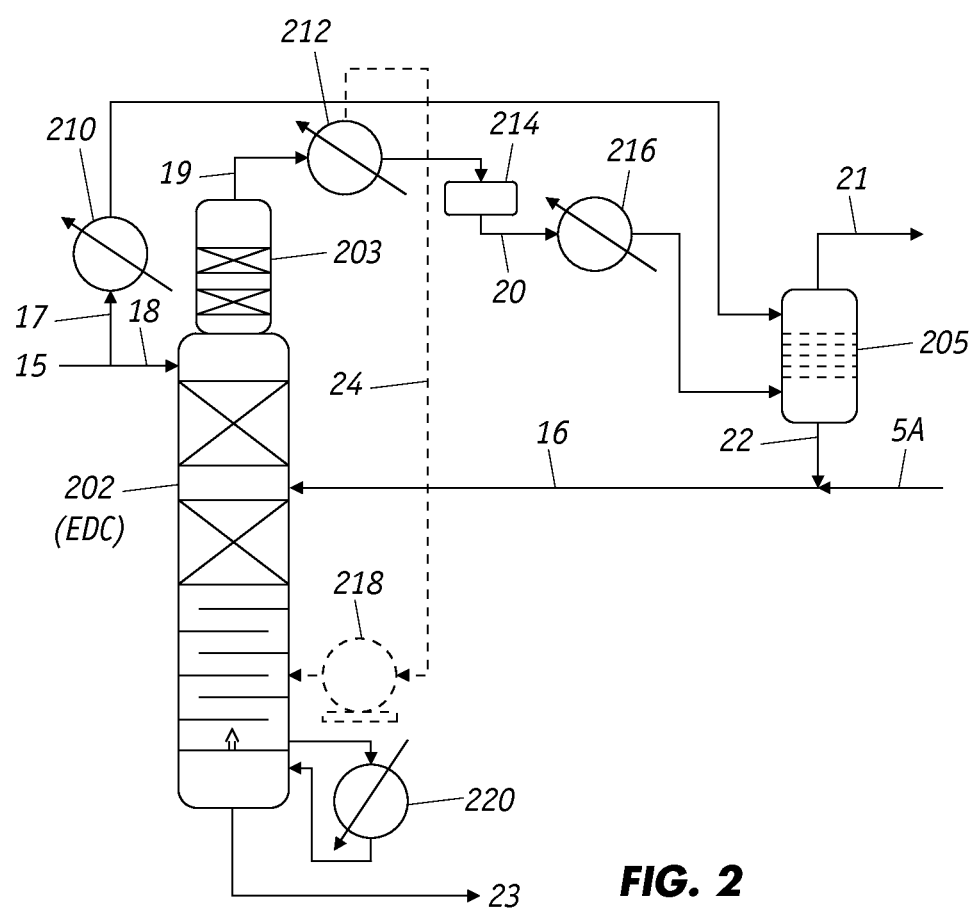
FIG. 2 is a schematic diagram of an improved ED process using a liquid-liquid extraction column for recovering additional benzene from the ED raffinate.
Figure 3:
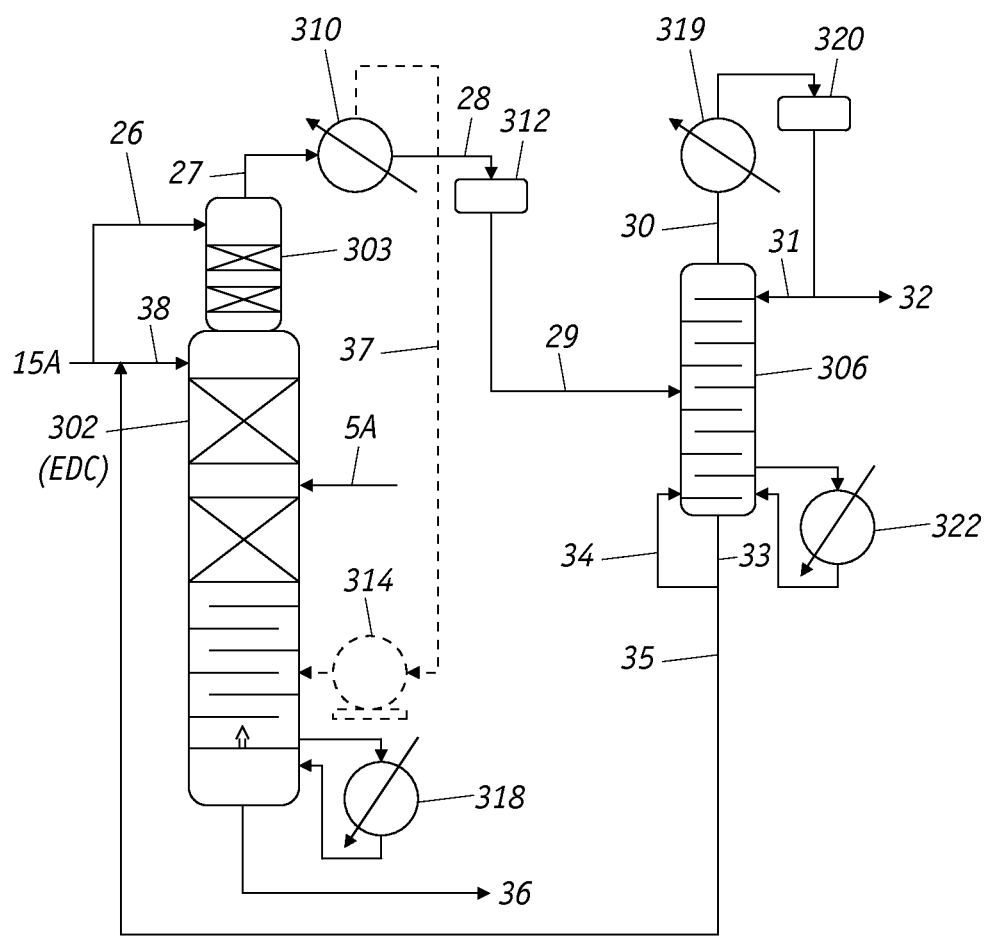
FIG. 3 is a schematic diagram of an improved ED process using a distillation column for recovering additional benzene from the ED raffinate.

In a conventional process, HDS unit 100 typically operates with reactor inlet and outlet temperatures of approximately, 230-235° C. and 250-255° C., respectively and under a reactor pressure of 28-29 Kg/cm² (gauge). Under these conditions, the concentration of MCH in the reactor effluent is controlled within a range of 1,500 to 2,500 ppm. If the end-of-run (EOR) reactor temperature is allowed to exceed 255° C. which leads to more MCH in the reactor effluent, the HDS catalyst regeneration cycle can be lengthened beyond 2 to 3 years, and subsequently, catalyst life can be prolonged beyond 3 to 5 years. With the present invention, it is possible to eliminate the restriction of generating excess MCH in HDS 100 unit by improving the operation of subsequent purification processes for a better separation between MCH and benzene as depicted in FIGS. 2 and 3.

As further shown in FIG. 1, a hydrotreated light fraction 2 from HDS unit is introduced to a $C_6$/$C_7$ splitter 101 where toluene and $C_7^+$ non-aromatics are removed from the bottom of the column via line 6, while the $C_6$ concentrate (which contains 90 to 98 wt %, preferably 96 to 98 wt % benzene and 2 to 10 wt %, preferably 2 to 4 wt % non-aromatics, including approximately 1,000 to 5,000 ppm MCH and preferably 2,500 to 5,000 ppm MCH) is withdrawn via line 3 from the top of the column 101, condensed through cooler 110, and transferred into accumulator 112. A portion of the condensate from 112 is recycled to the top of column 101 as the reflux through line 4 and the other portion is introduced via line 5 into the middle portion of the EDC 102.

A portion of the lean solvent from the bottom of the SRC 104 is fed to the upper portion of the EDC 102 via line 15 as the primary solvent feed. Raffinate vapor stream from the top of EDC 102 ascends into the raffinate distillation column 103 to separate the solvent and aromatic hydrocarbons (mainly benzene) from the non-aromatics. Conditions in the distillation column are adjusted so that a sump product recovering all the solvent in the raffinate, descends into the EDC 102 to provide an internal reflux to the top of EDC 102, while the overhead vapor from column 103 is transferred via line 7 and condensed in condenser 116 before entering accumulator 118. A portion of the solvent-free raffinate stream is recycled to the top of column 103 as reflux via 8 and the other portion is withdrawn as raffinate product through line 9. Rich solvent exiting the bottom of EDC 102 is transferred to the middle portion of SRC 104 via line 10.

Purified aromatic vapor is stripped from the solvent and withdrawn from the top of SRC 104 via line 12 and condensed in condenser 122 before entering accumulator 124. A portion of the aromatic hydrocarbon is recycled to the top of SRC 104 as reflux via line 13 and the other portion is withdrawn as the aromatic product (substantially all benzene) with trace of MCH through line 14. Lean solvent from the bottom of SRC 104 is recycled to upper part of EDC 102 via line 15.

The major consideration in operating EDC 102 and column 103 is to keep MCH away from the bottom of EDC 102 so that its concentration in the bottom benzene product can be maintained within specifications, without losing a substantial amount of benzene to the overhead raffinate product. Raffinate with high benzene concentration is less desired as a gasoline blending stock and cannot be used as a more valuable solvent; the presence of benzene in the raffinate also lowers the yield of benzene.

The present invention affords a simple and low cost process scheme that keeps MCH away from the bottom of EDC 102 and maintains the MCH content in the benzene product 14 in FIG. 1 to below 200 ppm, and reduces benzene concentration in the raffinate product taken from line 9 of FIG. 1, substantially from 40-50 wt % to 0-5 wt % and preferably to 0-2 wt %.

FIG. 2 depicts an improved ED process which employs a liquid-liquid extraction column to recover additional benzene from the ED raffinate. The hydrotreated $C_6$ concentrate from the overhead of splitter 101 (FIG. 1) is fed to the middle portion of EDC 202, that is equipped with reboiler 220, via lines 5A and 16, while lean solvent is fed to upper portion of EDC 202 via lines 15 and 18. Raffinate vapor stream from the top of EDC ascends into the integral raffinate distillation column 203 to separate the solvent and aromatic hydrocarbon (mainly benzene) from the non-aromatic hydrocarbons. By "integral" is meant that column 203 is constructed contiguous with or built within EDC 202 and no external piping is needed to connect the fluid flow between the two units. Conditions in column 203 are adjusted so that a sump product recovering all the solvent in the raffinate, which descends into the EDC to provide an internal reflux to the top of the EDC, while the overhead vapor from column 203 is transferred via line 19 and condensed in condenser 212 before entering accumulator 214.

The solvent-free raffinate stream withdrawn from 214 is cooled in cooler 216 and fed to the lower portion of liquid-liquid extraction (LLE) column 205 via line 20. Lean solvent in line 17, a slip stream from primary lean solvent line 15, is cooled in cooler 210 and fed to the upper portion of LLE column 205 to counter-currently extract benzene from the raffinate to reduce its benzene concentration substantially from 40-50 wt % to 0-5 wt %, preferably 0-2 wt %. The benzene reduced raffinate product is withdrawn from line 21 as a solvent-rich stream 22 is recovered from the bottom of LLE column 205 and recycled to EDC 202 via line 16. The ratio of lean solvent feed between the EDC and the LLE column preferably ranges from 50:1 to 150:1.

Because LLE column 205 can remove any amount of benzene from the raffinate stream to an extremely low level, the operation of the EDC 202 can focus primarily on driving essentially all the MCH from the bottom benzene product without concern with the loss of benzene to the raffinate. The cost of the LLE column operation is quite insignificant because weight ratio of the lean solvent between lines 15 and 17 is approximately 200:1, preferably 100:1, so the amount of solvent required by LLE column 205 is quite small. Also, the weight ratio of the hydrocarbons between line 16 (to EDC 202) and line 20 (to LLE column 205) is roughly 60:1 and preferably 40:1, so the diameter of LLE column 205 is quite small, only around 6 to 12 inches (15.2 to 30.4 cm) Furthermore, no additional energy is required for the LLE operation.

Optionally, the loading of upper portion of the EDC 202 can be increased by introducing an operational stripping agent to the lower portion of the EDC to prevent channeling in the upper portion of the EDC, including the integral part of column 203, thus, increasing their separation efficiencies. Overhead condenser 212 can be operated to condense only the raffinate to allow the stripping agent uncondensed and recycled to the lower portion of the EDC through line 24 and blower 218. The stripping agent is selected from the list comprising nitrogen, hydrogen, natural gas (methane), ethane, propane, $C_4$ and $C_5$ paraffins and combination thereof. A preferred stripping agent is natural gas and a particularly preferred stripping agent is nitrogen. Rich solvent exiting the bottom of EDC 202 is transferred to the middle portion of SRC 204 via line 23 to strip off the purified benzene product and recycle the lean solvent to EDC 202 through primary solvent line 15 via line 18.

The process shown in FIG. 2, exhibit, among other novel features: (1) preventing MCH accumulation in the raffinate distillation column (an integral upper portion of the EDC) by eliminating the external reflux of the EDC; (2) minimizing benzene loss to the overhead raffinate by contacting the raffinate with the lean solvent from a slip stream of the solvent loop in an extraction zone counter-currently to extract benzene from the raffinate stream; (3) recycling the extract phase from the extraction zone to the EDC at one or more entry points between the solvent feed and hydrocarbon feed entry points, and withdrawing the hydrocarbon phase as the raffinate product from the extraction zone without solvent removal; (4) optionally, increasing loading of upper portion of the EDC by introducing a stripping agent to the lower portion of the EDC to prevent channeling in the upper portion of the EDC, thus, increasing its separation efficiency; and (5) optionally, adjusting the overhead condenser for condensing only the raffinate to allow the stripping agent uncondensed, and recycling the gaseous stripping agent to the lower portion of the EDC through a blower.

FIG. 3 depicts the improved ED process which employs a distillation column to recover additional benzene from the ED raffinate. The hydrotreated $C_6$ concentrate from the overhead of splitter 101 (FIG. 1) is fed to the middle portion of EDC 302 via line 5A, and lean solvent that is supplied from the bottom of SRC 104 (FIG. 1) via lines 15A (from FIG. 1) and 38 is fed to the upper portion of EDC 302 which is equipped with reboiler 318. Raffinate vapor stream from the top of EDC ascends into integral raffinate distillation column 303 to separate the solvent and aromatic hydrocarbon (mainly benzene) from the non-aromatics. Conditions in column 303 are adjusted so that a sump product recovering most of all the solvent in the raffinate, which descends into EDC 302 to provide an internal reflux to the top of EDC 302. A slip stream of the lean solvent is fed to the top of column 303 via line 26 as a secondary solvent feed to assist the recovery of additional benzene from the raffinate vapor at the top of column 303. The benzene-free (or benzene reduced) overhead vapor from column 303 is transferred via line 27 and condensed in condenser 310 before entering accumulator 312 via line 28.

The raffinate equivalent to 2 to 4 wt % of the feedstock to EDC 302 is withdrawn from accumulator 312 and introduced to the middle portion of distillation column 306 via line 29 to remove the trace amount of entrained solvent from the bottoms of said column, which is circulated in a closed loop around the column bottom through lines 33 and 34. A slip stream is withdrawn from the loop via line 35, which is then combined with the primary lean solvent stream and fed to the top of EDC 320 via line 38. A solvent-free raffinate vapor stream is recovered from the top of column 306, condensed in cooler 319 and introduced to accumulator 320 via line 30. A portion of the raffinate from accumulator 320 is recycled to the top of column 306 as the reflux through line 31, while the other portion is withdrawn as the raffinate product via line 32. The size of distillation column 306, which is equipped reboiler 322, is substantially smaller than that of the major columns 302 and 303, so its operational costs are comparatively lower.

Again, because distillation column 303 functions like an EDC with a secondary solvent to recover any amount of benzene from the raffinate stream to an extremely low level, and distillation column 306, which equipped with roboiler 322, eliminates any entrained solvent from the raffinate product, the operation of EDC 302 can focus on driving essentially all the MCH from the bottom benzene product without concern with loss of benzene to the raffinate.

As an optionally, loading of tipper portion of EDC 302 can be increased by introducing a stripping agent to the lower portion of the EDC to prevent channeling in the upper portion of EDC 302 as well as the integral raffinate distillation column 303, thus, increasing their separation efficiencies. Overhead condenser 310 can be operated to condense only the raffinate to allow the stripping agent uncondensed and recycled to the lower portion of the EDC through line 37 and blower 314. The operational stripping agent is selected from the list comprising nitrogen, hydrogen, natural gas (methane), ethane, propane, $C_4$ and $C_5$ paraffins, and the combination thereof. A referred stripping agent is natural gas and particularly preferred stripping agent is nitrogen. Rich solvent exiting the bottom of EDC 302 is transferred to the middle portion of SRC 104 (FIG. 1) via line 36 to strip off the purified benzene product and recycle the lean solvent to EDC 302 through line 15A.

The process shown in FIG. 3 exhibit, among other novel features: (2) preventing MCH accumulation in the raffinate distillation column by eliminating the external reflux to the EDC; (2) minimizing benzene loss to the overhead raffinate by feeding a secondary solvent feed to the top of the integral raffinate distillation column (at the original external reflux entry point) and by reducing the reboiler duty; (3) optionally, increasing loading of upper portion of the EDC by introducing a stripping agent to lower portion of the EDC to prevent channeling in upper portion of the EDC, thus, increasing its separation efficiency; (4) optionally, adjusting the overhead condenser for condensing only the raffinate to allow the stripping agent uncondensed, and recycling the gaseous stripping agent to lower portion of the EDC through a blower; (5) feeding liquid raffinate (from the overhead accumulator) to a small separate distillation column and withdrawing the solvent-free raffinate product from the overhead of said distillation column and circulating the bottom stream of said distillation column in a closed loop between reboiler and the bottom of the column; and (6) withdrawing a slip stream from the bottom loop of said distillation column and recycling said stream to the EDC with the solvent feed.

EXAMPLES

The following examples further illustrate different aspects and embodiments of the invention and are not to be considered as limiting the scope of the invention.

Example 1

To demonstrate effectiveness the of N-formyl morpholine (NFM) as a selective solvent for extracting benzene from overhead stream of the raffinate distillation column 203 (which an integrated upper part of EDC 202) shown in FIG. 2, extraction experiment was conducted in laboratory using a glass separatory funnel. A sample of the overhead raffinate stream was analyzed in a gas chromatography/mass spectrometer (GC/MS) analyzer and the composition of the stream is summarized in Table 1.

TABLE 1

Composition of Overhead Raffinate from Column 203/EDC 202

| Component | Wt % | Component | Wt % |
|---|---|---|---|
| i-Pentane | 0.49 | n-Pentane | 1.75 |
| Cyclopentane | 31.79 | 2-Methyl Pentane | 0.38 |
| 3-Methyl Pentane | 0.23 | n-Hexane | 0.94 |
| Methylcyclopentane | 4.33 | Benzene | 45.11 |
| Cyclohexane | 6.06 | 2-Methyl Hexane | 0.18 |
| Dimethylcyclopentanes | 1.43 | 3-Methyl Hexane | 0.26 |
| n-Heptane | 1.72 | Methylcyclohexane | 4.07 |
| Ethylcyclopentane | 0.90 | Trimethyl Pentanes | 0.30 |

The analysis demonstrated that the overhead raffinate stream, besides containing benzene, is extremely rich in cyclic paraffins, including cyclopentane, cyclohexane, and MCH. The NFM solvent for this test was obtained from the lean solvent of a commercial ED plant wherein NFM was used as the selective solvent for recovering high purity benzene from hydrotreated $C_6$ fraction of coal tar. This NFM solvent contained more than 97 wt % NFM and less than 3 wt % benzene with essentially no other impurities.

Approximately 360.0 grams of the NFM solvent and 180.0 grams of the raffinate with composition shown in Table 1, under a solvent-to-feed weight ratio (S/F) of 2:1, were added to a separatory funnel and well mixed to create two liquid phases after settling at room temperature. The liquid phases were then separated and samples of both the raffinate (hydrocarbon) phase and the extract (solvent) phase were analyzed to yield the compositions in Tables 2 and 3, respectively:

TABLE 2

Composition of Raffinate Phase from Extraction with 2.0 of Solvent-to-Feed Ratio

| Component | Wt % | Wt %* | Component | Wt % | Wt %* |
|---|---|---|---|---|---|
| i-Pentane | 0.72 | 0.73 | n-Pentane | 2.62 | 2.67 |
| Cyclopentane | 40.67 | 41.44 | 2-Methyl Pentane | 0.63 | 0.64 |
| 3-Methyl Pentane | 0.37 | 0.38 | n-Hexane | 1.59 | 1.62 |
| Methylcyclopentane | 6.37 | 6.49 | Benzene | 21.77 | 22.18 |
| Cyclohexane | 8.77 | 8.94 | 2-Methyl Hexane | 0.33 | 0.34 |
| Dimethylcyclopentanes | 1.55 | 1.58 | 3-Methyl Hexane | 0.47 | 0.48 |
| 3-Ethyl Pentane | 0.32 | 0.33 | n-Heptane | 3.16 | 3.22 |
| Methylcyclohexane | 6.55 | 6.67 | Dimehtylhexanes | 0.25 | 0.25 |
| Ethylcyclopentane | 1.46 | 1.49 | Trimethyl Pentanes | 0.21 | 0.21 |
| NFM (Solvent) | 1.90 | | | | |

*Composition on a solvent-free basis

TABLE 3

Composition of Extract Phase from Extraction with 2.0 Solvent-to-Feed ratio

| Component | Wt % | Wt %* | Component | Wt % | Wt %* |
|---|---|---|---|---|---|
| i-Pentane | 0.14 | 0.28 | n-Pentane | 0.51 | 1.04 |
| Cyclopentane | 12.03 | 24.42 | 2-Methyl Pentane | 0.10 | 0.20 |
| 3-Methyl Pentane | 0.06 | 0.12 | n-Hexane | 0.25 | 0.51 |
| Methylcyclopentane | 1.45 | 2.94 | Benzene | 29.90 | 60.70 |
| Cyclohexane | 2.08 | 4.22 | Dimethylcyclopentanes | 0.27 | 0.55 |
| 3-Methyl Hexane | 0.19 | 0.39 | n-Heptane | 0.40 | 0.81 |
| Methylcyclohexane | 1.23 | 2.50 | Ethylcyclopentane | 0.27 | 0.55 |
| NFM (Solvent) | 50.78 | | | | |

*Composition on a solvent-free basis

Based on the experimental data from a one-theoretical stage extraction under a S/F of 2.0 as presented in Tables 2 and 3, the separation factor (SF) between MCH and benzene (BZ) on solvent-free phase compositions can be as high as 7.3 according to the following calculation:

$$SF = \frac{[(MCH \text{ in Raffinate})/(MCH \text{ in Extract})]}{[(BZ \text{ in Raffinate})/(BZ \text{ in Extract})]}$$

$$= [(6.67)/(2.50)]/[(22.18)/(60.70)]$$

$$= 7.3$$

This result suggests that NFM solvent is very effective in extracting benzene from the EDC overhead raffinate stream, in which the non-aromatic hydrocarbons are mainly cycloparaffins, including MCH, which have higher polarities than other types of non-aromatic hydrocarbons.

Example 2

To test the effect of the solvent-to-feed ratio on the separation factor for separating benzene and cycloparaffins, especially MCH, the lab experimental procedures of Example 1 were repeated under S/F of 1.0, 4.0, 5.0, and 6.0. The test results are summarized in Tables 4 to 9.

TABLE 4

Composition of Raffinate Phase from Extraction with 1.0 of Solvent-to-Feed Ratio

| Component | Wt % | Wt %* | Component | Wt % | Wt %* |
|---|---|---|---|---|---|
| i-Pentane | 0.60 | 0.62 | n-Pentane | 2.19 | 2.27 |
| Cyclopentane | 36.79 | 38.08 | 2-Methyl Pentane | 0.51 | 0.53 |
| 3-Methyl Pentane | 0.31 | 0.32 | n-Hexane | 1.29 | 1.34 |
| Methylcyclopentane | 5.46 | 5.65 | Benzene | 29.92 | 30.97 |
| Cyclohexane | 7.58 | 7.85 | 2-Methyl Hexane | 0.26 | 0.27 |
| Dimethylcyclopentanes | 1.26 | 1.30 | 3-Methyl Hexane | 0.46 | 0.48 |
| 3-Ethyl Pentane | 0.25 | 0.26 | n-Heptane | 2.47 | 2.56 |
| Methylcyclohexane | 5.43 | 5.62 | Dimehtylhexanes | 0.19 | 0.20 |
| Ethylcyclopentane | 1.20 | 1.24 | Trimethyl Pentanes | 0.23 | 0.24 |
| NFM (Solvent) | 3.37 | | | | |

*Composition on a solvent-free basis

TABLE 5

Composition of Extract Phase from Extraction with 1.0 of Solvent-to-Feed Ratio

| Component | Wt % | Wt %* | Component | Wt % | Wt % |
|---|---|---|---|---|---|
| i-Pentane | 0.17 | 0.28 | n-Pentane | 0.62 | 1.01 |
| Cyclopentane | 14.43 | 23.59 | 2-Methyl Pentane | 0.13 | 0.22 |
| 3-Methyl Pentane | 0.08 | 0.13 | n-Hexane | 0.32 | 0.52 |
| Methylcyclopentane | 1.77 | 2.89 | Benzene | 37.86 | 61.90 |
| Cyclohexane | 2.54 | 4.15 | Dimethylcyclopentanes | 0.34 | 0.56 |
| 3-Methyl Hexane | 0.22 | 0.36 | n-Heptane | 0.52 | 0.85 |
| Methylcyclohexane | 1.53 | 2.50 | Ethylcyclopentane | 0.33 | 0.54 |
| NFM (Solvent) | 38.85 | | | | |

*Composition on a solvent-free basis

TABLE 6

Composition of Raffinate Phase from Extraction with 4.0 of Solvent-to-Feed Ratio

| Component | Wt % | Wt %* | Component | Wt % | Wt %* |
|---|---|---|---|---|---|
| i-Pentane | 0.84 | 0.85 | n-Pentane | 3.08 | 3.12 |
| Cyclopentane | 41.97 | 42.52 | 2-Methyl Pentane | 0.79 | 0.80 |
| 3-Methyl Pentane | 0.46 | 0.47 | n-Hexane | 2.02 | 2.05 |
| Methylcyclopentane | 7.18 | 7.27 | Benzene | 14.59 | 14.78 |
| Cyclohexane | 9.757 | 9.88 | 2-Methyl Hexane | 0.44 | 0.45 |
| Dimethylcyclopentanes | 1.89 | 1.91 | 3-Methyl Hexane | 0.44 | 0.45 |
| 3-Ethyl Pentane | 0.42 | 0.43 | n-Heptane | 4.27 | 4.33 |
| Methylcyclohexane | 7.86 | 7.96 | Dimehtylhexanes | 0.32 | 0.32 |
| Ethylcyclopentane | 1.76 | 1.78 | Trimethyl Pentanes | 0.29 | 0.29 |
| NFM (Solvent) | 1.26 | | | | |

*Composition on a solvent-free basis

TABLE 7

Composition of Extract Phase from Extraction with 4.0 of Solvent-to-Feed Ratio

| Component | Wt % | Wt %* | Component | Wt % | Wt % |
|---|---|---|---|---|---|
| i-Pentane | 0.13 | 0.33 | n-Pentane | 0.48 | 1.22 |
| Cyclopentane | 10.71 | 27.29 | 2-Methyl Pentane | 0.10 | 0.25 |
| 3-Methyl Pentane | 0.06 | 0.15 | n-Hexane | 0.25 | 0.64 |
| Methylcyclopentane | 1.36 | 3.47 | Benzene | 21.68 | 55.24 |
| Cyclohexane | 1.93 | 6.85 | Dimethylcyclopentanes | 0.17 | 0.43 |
| 3-Methyl Hexane | 0.16 | 0.41 | n-Heptane | 0.41 | 1.04 |
| Methylcyclohexane | 1.19 | 3.03 | Ethylcyclopentane | 0.26 | 0.66 |
| NFM (Solvent) | 60.75 | | | | |

*Composition on a solvent-free basis

TABLE 8

Composition of Raffinate Phase from Extraction with 5.0 of Solvent-to-Feed Ratio

| Component | Wt % | Wt %* | Component | Wt % | Wt %* |
|---|---|---|---|---|---|
| i-Pentane | 0.82 | 0.83 | n-Pentane | 3.07 | 3.10 |
| Cyclopentane | 41.89 | 42.31 | 2-Methyl Pentane | 0.85 | 0.86 |
| 3-Methyl Pentane | 0.50 | 0.51 | n-Hexane | 2.21 | 2.23 |
| Methylcyclopentane | 7.47 | 7.54 | Benzene | 12.11 | 12.23 |
| Cyclohexane | 10.17 | 10.27 | 2-Methyl Hexane | 0.50 | 0.51 |
| Dimethylcyclopentanes | 2.09 | 2.11 | 3-Methyl Hexane | 0.43 | 0.43 |
| 3-Ethyl Pentane | 0.48 | 0.48 | n-Heptane | 4.93 | 4.33 |
| Methylcyclohexane | 8.58 | 8.67 | Dimethylhexanes | 0.35 | 0.35 |

TABLE 8-continued

Composition of Raffinate Phase from Extraction
with 5.0 of Solvent-to-Feed Ratio

| Component | Wt % | Wt %* | Component | Wt % | Wt %* |
|---|---|---|---|---|---|
| Ethylcyclopentane | 1.92 | 1.94 | Trimethyl Pentanes | 0.22 | 0.22 |
| NFM (Solvent) | 1.01 | | | | |

*Composition on a solvent-free basis

TABLE 9

Composition of Extract Phase from Extraction with
5.0 of Solvent-to-Feed Ratio

| Component | Wt % | Wt %* | Component | Wt % | Wt % |
|---|---|---|---|---|---|
| i-Pentane | 0.12 | 0.35 | n-Pentane | 0.42 | 1.21 |
| Cyclopentane | 9.51 | 27.39 | 2-Methyl Pentane | 0.10 | 0.29 |
| 3-Methyl Pentane | 0.06 | 0.17 | n-Hexane | 0.23 | 0.66 |
| Methylcyclopentane | 1.25 | 3.60 | Benzene | 18.63 | 53.65 |
| Cyclohexane | 1.79 | 5.16 | Dimethylcyclo-pentanes | 0.16 | 0.46 |
| 3-Ethylpentane | 0.18 | 0.52 | n-Heptane | 0.39 | 1.12 |
| Methylcyclohexane | 1.13 | 3.25 | Ethylcyclopentane | 0.25 | 0.72 |
| NFM (Solvent) | 65.28 | | | | |

*Composition on a solvent-free basis

From the experimental results for the raffinate and extract phase compositions that were derived under different solvent-to-feed ratios, the separation factors between MCH and benzene were next calculated in accordance with the previously defined SF formula. The results are summarized in Table 10.

TABLE 10

Separation Factor Between MCH and Benzene versus S/F of Extraction

| S/F (solvent-to-feed weight ratio) | SF (separation factor) |
|---|---|
| 1.0 | 4.49 |
| 2.0 | 7.30 |
| 4.0 | 9.82 |
| 5.0 | 11.70 |

As expected, a higher solvent-to-feed ratio yields a higher the separation factor but the incremental increase diminishes at higher S/F ratios. Another important observation from this investigation is that a clean phase separation can be achieved between the raffinate and the extract phases even under a high solvent-to-feed weight ratio (S/F=5.0), although the non-aromatic components of the hydrocarbon feed, which are primarily the more polar cycloparaffins, tend to dissolve into the solvent phase and cause difficulty in phase separation. Nevertheless, under an S/F of 6.0 or higher, it was found that no phase separation could be formed since the hydrocarbon feed mixture was totally dissolved in the solvent phase.

Example 3

The test results from Examples 1 and 2 were incorporated into a simulation model of the process illustrated in FIG. 2 and employed to design an improved process for recovering high purity benzene with acceptable an MCH content from a hydrotreated $C_6$ fraction of coal tar or other similar feedstock that features various aspects of the invention. Specifically, referring to FIG. 2, a NFM solvent feed that is at temperature in the range of 90 to 110° C. is fed to the upper portion of EDC 202 via lines 15 and 18 at a rate of approximately 21,600 kg/hr, while roughly 3,700 kg/hr of a hydrotreated $C_6$ fraction from the top of splitter column 201 is introduced to the middle portion of EDC 202 through lines 5A and 16 at temperature in the range of 70 to 90° C. Reboiler 220 of EDC 202 is operated at a temperature range of 130 to 150° C. to drive substantially all of the MCH from the bottom rich solvent, which consists of essentially pure benzene and the solvent, and exits the bottom of EDC 202 via line 23 at a rate of approximately 25,500 kg/hr. Raffinate vapor from the top of column 203 which contains excess amounts of aromatics that consists mainly benzene (about 48 wt %) is condensed through condenser 212 and transferred to accumulator 214 at a rate 110 kg/hr at a temperature in the range of 70 to 80° C. via line 19. Column 203 is an integral part of the upper distillation portion of EDC 202.

A raffinate stream which withdrawn from the bottom of accumulator 214 is further cooled to approximately 40° C. in cooler 216 and fed to the lower portion of LLE column 210. A slip stream of 225 kg/hr from the lean solvent feed via line 17 is cooled through cooler 210 to 40° C. and fed to the upper portion of LLE column 205 to counter-currently extract aromatics (mainly benzene) from the raffinate stream. A raffinate product via line 21 is withdrawn at a rate in the range of 50 to 60 kg/hr from the top of column 205 and it contains 1.0 to 2.0 wt % benzene with no more than 0.5 wt % solvent. An extract stream from column 205 containing roughly 80 wt % solvent, 20 wt % aromatics (mainly benzene) and less than 1 wt % non-aromatics is taken from the column bottom through line 22 at a flow rate in the range of 270 to 290 kg/hr. This stream is then combined with the EDC hydrocarbon feed from line 5A (FIG. 1) and fed to the middle portion of EDC 202 via line 16. The composition of the feed stream in line 16 contains 93 to 95 wt % aromatics (benzene), 1 to 2 wt % non-aromatics, and about 5 wt % solvent.

This example demonstrates that with the improved process 1 wt % of the lean solvent (225 kg/hr) is sufficient to extract benzene in the raffinate stream and to reduce its benzene concentration from as high as 50 wt % to less than 2 wt % even when using in a very small extraction column that is 8 inches (20.3 cm) in diameter with no extra energy requirements. Benzene that is recovered in the extract phase is recycled back to EDC 202.

The configuration of this low-cost raffinate extraction column affords a number of process benefits. First, the HDS unit 100 (FIG. 1) can operate under conditions to maximize desulfurization and denitrogenation of the hydrocarbon feed without impeded by the undesirable generation of MCH from the non-selective hydrogenation of toluene; consequently, the HDS requires lower catalyst activity and fewer catalyst replacements. Second, EDC 202 (FIG. 2) can operate with fewer restrictions in order drive essentially all the MCH into the overhead raffinate stream and away from the bottom product, benzene. Moreover, excess amounts of benzene in the raffinate can be readily recovered and recycled by low-cost LLE column 205.

Example 4

Sulfolane is another important extraction solvent for recovering aromatic hydrocarbons from reformate and pyrolysis gasoline, although it is not commonly used in the ED process for benzene recovery from the hydrotreated $C_6$ fraction of coal tar. To demonstrate the effectiveness of sulfolane for extracting benzene from the overhead stream of the raffinate distillation column 203 (which is an integral upper part of EDC 202) shown in FIG. 2, an extraction experiment was conducted in a laboratory separatory funnel which is equivalent to one-theoretical extraction stage.

The sulfolane solvent for this test was obtained from the lean solvent of a commercial extractor for recovering benzene, toluene, and xylenes from pyrolysis gasoline. This solvent contained 98.5 wt % sulfolane (analyzed on water-free basis) and less than 0.8 wt % water. Approximately 300.0 grams of the sulfolane solvent and 75.0 grams of the raffinate with composition shown in Table 1, under a solvent-to-feed weight ratio (S/F) of 4:1, was added to the separatory funnel and well mixed to create two liquid phases after settling at room temperature. The liquid phases were then separated and samples of both the raffinate (hydrocarbon) phase and the extract (solvent) phase were analyzed to yield the compositions in Tables 11 and 12, respectively:

TABLE 11

Composition of Raffinate Phase Extracted with the Sulfolane Solvent Under S/F of 4.0

| Component | Wt % | Wt %* | Component | Wt % | Wt %* |
|---|---|---|---|---|---|
| i-Pentane | 0.71 | 0.71 | n-Pentane | 2.60 | 2.61 |
| Cyclopentane | 42.39 | 42.60 | 2-Methyl Pentane | 0.62 | 0.62 |
| 3-Methyl Pentane | 0.38 | 0.38 | n-Hexane | 1.59 | 1.60 |
| Methylcyclopentane | 6.65 | 6.68 | Benzene | 16.50 | 16.58 |
| Cyclohexane | 9.23 | 9.28 | 2-Methyl Hexane | 0.32 | 0.32 |
| Dimethylcyclopentanes | 1.59 | 1.60 | 3-Methyl Hexane | 0.50 | 0.50 |
| 3-Ethyl Pentane | 0.32 | 0.32 | n-Heptane | 3.13 | 3.15 |
| Methylcyclohexane | 6.83 | 6.86 | Dimehtylhexanes | 0.26 | 0.26 |
| Ethylcyclopentane | 1.52 | 1.52 | Trimethyl Pentanes | 0.16 | 0.16 |
| Sulfolane (Solvent) | 0.46 | | Unknown | | 4.25 |

*Composition on a solvent-free basis

TABLE 12

Composition of Extract Phase Extracted with the Sulfolane Solvent Under S/F of 4.0

| Component | Wt % | Wt %* | Component | Wt % | Wt % |
|---|---|---|---|---|---|
| i-Pentane | 0.03 | 0.13 | n-Pentane | 0.12 | 0.53 |
| Cyclopentane | 4.05 | 18.01 | 2-Methyl Pentane | 0.00 | 0.00 |
| 3-Methyl Pentane | 0.01 | 0.04 | n-Hexane | 0.05 | 0.22 |
| Methylcyclopentane | 0.42 | 1.87 | Benzene | 16.11 | 71.63 |
| Cyclohexane | 0.63 | 2.80 | Dimethylcyclopentanes | 0.06 | 0.27 |
| 3-Ethylpentane | 0.08 | 0.36 | n-Heptane | 0.08 | 0.36 |
| Methylcyclohexane | 0.32 | 1.42 | Ethylcyclopentane | 0.07 | 0.31 |
| Sulfolane (Solvent) | 77.51 | | Unknown | | 2.05 |

*Composition on a solvent-free basis

From the compositions of the raffinate and extract phases shown in Tables 11 and 12, the separation factor (SF) between MCH and benzene under the extraction of sulfolane (with 0.8 wt % water) is determined to be 20.87. From the separation factor at a 4.0 solvent-to-feed weight ratio, it appears that the sulfolane solvent is more selective than the NFM solvent in recovering benzene from the mixture containing benzene and the cycloparaffins, including MCH.

The boiling point of sulfolane is significantly higher that of the NFM solvent. Stream stripping is normally used to separate the aromatic (benzene) product from the sulfolane solvent, in order to minimize the reboiler temperature in the solvent recovery column (SRC). An extraction process using the sulfolane solvent should be equipped with water circulation system to supply the stripping steam in SRC and to maintain the water content in the sulfolane solvent.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A process for recovering high purity benzene from a feedstock containing aromatic hydrocarbons and non-aromatic hydrocarbons that comprises the steps of:
   (a) removing sulfur and nitrogen contaminants from the feedstock through a hydrodesulfurization (HDS) unit to yield a hydrotreated feedstock;
   (b) introducing the hydrotreated feedstock into in a distillation column to remove a heavy portion of the hydrotreated feedstock and to recover a $C_6$ fraction and lighter portion of the hydrotreated feedstock that contains benzene which is introduced to a middle portion of an extractive distillation column (EDC);
   (c) introducing a lean solvent stream that is recycled from the bottom of a solvent recovery column (SRC) into an upper portion of the EDC as a selective solvent feed;
   (d) recovering a first non-aromatic hydrocarbon-rich stream from the top of the EDC and withdrawing a first solvent-rich stream containing the solvent and substantially all the benzene that was present in the $C_6$ fraction and lighter portion of the hydrotreated feedstock from the bottom of the EDC;
   (e) introducing the first solvent-rich stream into a middle portion of the SRC and recovering an aromatic hydrocarbon stream consisting essentially of benzene and that is substantially free of the solvent and non-aromatic hydrocarbons from the top of the SRC and removing the lean solvent stream from the bottom of the SRC;
   (f) introducing the first non-aromatic hydrocarbon-rich stream from step (d) into a lower portion of a liquid-liquid extraction (LLE) column and introducing a slip stream from the lean solvent stream from step (c) into an upper portion of the LLE column as the solvent feed stream; and
   (g) recovering a second non-aromatic hydrocarbon-rich stream from the top of the LLE column as a raffinate product and removing a second solvent-rich stream from the bottom of the LLE column, which is recycled into the middle portion of the EDC wherein the LLE column is operated under conditions to achieve 0 to 2 wt % benzene in the second non-aromatic hydrocarbon-rich stream through extraction of benzene from the first non-aromatic hydrocarbon-rich stream which contains higher than 50 wt % benzene.

2. The process of claim 1 further comprising step (h) of introducing a stripping agent into a lower portion of the EDC, which is below the middle portion of the EDC where the hydrotreated feedstock is introduced to prevent channeling in an upper portion of the EDC that is caused by low column loading to thereby enhance its separation efficiency.

3. The process of claim 1 wherein the feedstock is coal tar containing $C_5$ to $C_7$ hydrocarbons.

4. The process of claim 1 wherein the HDS unit is operated under conditions that generate hydrotreated feedstock that contains less than 0.1 ppm sulfur and nitrogen and without modifications of the conditions to account for undesirable production of methylcyclohexane (MCH) through non-selective hydrogenation.

5. The process of claim 4 wherein the HDS unit has an outlet temperature higher than 255° C. and yields a hydrotreated feedstock with an MCH content that ranges from 2,500 to 5,000 ppm.

6. The process of claim 1 wherein each of the lean solvent stream to the EDC and slip stream to the LLE column comprises a lean solvent that is selected from the group consisting of N-substituted morpholines with substituents containing not more than 7 carbon atoms, sulfolane, glycols, N-methyl pyrrolidone and mixtures thereof.

7. The process of claim 6 wherein the lean solvent is N-formyl morpholine (NFM).

8. The process of claim 6 wherein the lean solvent is sulfolane that contains 0 to 1.0 wt % water.

9. The process of claim 1 wherein the ratio of lean solvent feed between the EDC and the LLE column is 50:1 to 150:1.

10. The process of claim 1 wherein the EDC is operated under conditions to achieve a 0 to 50 ppm MCH content in the first solvent-rich stream from the bottom of the EDC, without having to modify the conditions to account for the benzene content in the first non-aromatic hydrocarbon-rich stream from the top of the EDC.

11. The process of claim 1 wherein an upper portion of the EDC contains a raffinate distillation column which is an integral part of the EDC for separating the solvent and a portion of benzene from the ascending raffinate vapor stream to provide an internal reflux to upper part of the EDC.

12. The process of claim 2 wherein the stripping agent is selected from the group consisting of nitrogen, hydrogen, natural gas (methane), ethane, propane, $C_4$ and $C_5$ paraffins and mixtures thereof.

13. The process of claim 12 wherein the stripping agent is nitrogen.

14. A process for recovering high purity benzene from a feedstock containing aromatic hydrocarbons and non-aromatic hydrocarbons that comprises the steps of:
  (a) removing sulfur and nitrogen contaminants from the feedstock through a hydrodesulfurization (HDS) unit to yield a hydrotreated feedstock;
  (b) introducing the hydrotreated feedstock into a distillation column to remove a heavy portion of the hydrotreated feedstock and to remove a $C_6$ fraction and lighter portion of the feedstock which is introduced into a middle portion of an EDC which contains a raffinate distillation column as an integral upper portion of the EDC for recovering benzene from ascending raffinate vapor stream to provide an internal reflux for the EDC;
  (c) introducing a lean solvent stream recycled from the bottom of a solvent recovery column (SRC) into an upper portion of the EDC below the raffinate distillation column as a primary selective solvent feed;
  (d) introducing a slip stream from the primary selective solvent stream to the upper portion of the raffinate distillation column in step (b) as a secondary selective solvent feed to convert the raffinate distillation column into an auxiliary EDC to recover additional benzene from a first non-aromatic hydrocarbon-rich stream;
  (e) recovering the first non-aromatic hydrocarbon-rich stream that is low in benzene content from the top of the EDC and withdrawing a first solvent-rich stream containing the solvent and substantially pure benzene from the bottom of the EDC;
  (f) introducing the first solvent-rich stream into a middle portion of the SRC, recovering an aromatic hydrocarbon stream containing essentially pure benzene, that is substantially free of the solvent and non-aromatic hydrocarbons, from the top of the SRC, and removing the lean solvent stream from the bottom of the SRC; and
  (g) introducing the first non-aromatic hydrocarbon-rich stream into a middle portion of a distillation column to recover a second non-aromatic hydrocarbon-rich stream from the top of the distillation column as a raffinate product, and to remove a bottom stream from said distillation column containing benzene, non-aromatic hydrocarbons and entrained solvent, which is recycled to the EDC as a mixture with the EDC primary solvent, feed stream wherein the distillation column is operated under conditions to achieve less than 1 ppm solvent in the second non aromatic hydrocarbon-rich stream through removal of entrained solvent from the first non-aromatic hydrocarbon-rich stream which contains 0 to 2.0 wt % benzene.

15. The process of claim 14 further comprising step (h) of introducing a stripping agent to the lower portion of the EDC, which is below the middle portion of the EDC where the hydrotreated feedstock is introduced, to prevent channeling in an upper portion of the EDC caused by low column loading, to increase its separation efficiency.

16. The process of claim 14 wherein the feedstock is coal tar containing $C_5$ to $C_7$ hydrocarbons.

17. The process of claim 14 wherein the HDS unit is operated under conditions that generate hydrotreated feedstock that contains less than 1 ppm sulfur and nitrogen and without modifications of the conditions to account for undesirable production of methylcyclohexane (MCH) through non-selective hydrogenation.

18. The process of claim 17 wherein the unit has an outlet temperature higher than 255° C. and yields a hydrotreated feedstock with MCH content that ranges from 2,500 to 5,000 ppm.

19. The process of claim 14 wherein the lean solvent stream for the EDC comprises lean solvent that is selected from the group consisting of N-substituted morpholines with substituents containing not more than 7 carbon atoms, sulfolane, glycols, N-methyl pyrrolidone and mixtures thereof.

20. The process of claim 19 wherein the lean solvent is N-formyl morpholine (NFM).

21. The process of claim 19 wherein the lean solvent is sulfolane that contains 0 to 1.0 wt % water.

22. The process of claim 14 wherein the EDC is operated under conditions to achieve an MCH concentration of 0 to 50 ppm in the first solvent-rich stream from the bottom of the EDC.

23. The process of claim 15 wherein the stripping agent is selected from the group consisting of nitrogen, hydrogen, natural gas (methane), ethane, propane $C_4$ and $C_5$ paraffins and mixtures thereof.

24. The process of claim 23 wherein the stripping agent is nitrogen.

* * * * *